US012617572B2

(12) United States Patent
Yu et al.

(10) Patent No.: US 12,617,572 B2
(45) Date of Patent: May 5, 2026

(54) FULLY AUTOMATED FILLING LINE FOR TISSUE CULTURE FLASKS AND CONTROL METHOD THEREFOR

(71) Applicant: Zhejiang Academy of Agricultural Sciences, Hangzhou (CN)

(72) Inventors: Guohong Yu, Hangzhou (CN); Hang Zheng, Hangzhou (CN); Xianglei Xue, Hangzhou (CN); Yunxiang Ye, Hangzhou (CN); Tian Liu, Hangzhou (CN); Ning Ren, Hangzhou (CN)

(73) Assignee: Zhejiang Academy of Agricultural Sciences, Hangzhou (CN)

( * ) Notice: Subject to any disclaimer, the term of this patent is extended or adjusted under 35 U.S.C. 154(b) by 0 days.

(21) Appl. No.: 19/246,946

(22) Filed: Jun. 24, 2025

(65) Prior Publication Data

US 2025/0368371 A1 Dec. 4, 2025

(30) Foreign Application Priority Data

Jan. 8, 2025 (CN) .......................... 202510025810.0

(51) Int. Cl.
| | |
|---|---|
| B65B 55/24 | (2006.01) |
| A01H 4/00 | (2006.01) |
| B65B 55/02 | (2006.01) |
| B65B 57/02 | (2006.01) |
| B65B 57/04 | (2006.01) |

(Continued)

(52) U.S. Cl.
CPC ............. B65B 55/24 (2013.01); A01H 4/001 (2013.01); B65B 55/02 (2013.01); B65B 55/025 (2013.01);

(Continued)

(58) Field of Classification Search
CPC ....... B65B 55/02; B65B 55/025; B65B 55/24; B65B 57/02; B65B 57/04; B67C 3/007;

(Continued)

(56) References Cited

U.S. PATENT DOCUMENTS

| 4,761,936 A | * | 8/1988 | Suzuki et al. | ......... | C12M 29/00 |
| | | | | | 53/425 |
| 5,016,688 A | * | 5/1991 | Suzuki et al. | ......... | C12M 29/00 |
| | | | | | 53/425 |

(Continued)

FOREIGN PATENT DOCUMENTS

| CN | 117502244 A | * | 2/2024 | ............. | A01H 4/001 |
| CN | 117923404 A | * | 4/2024 | ............. | A01H 4/001 |

OTHER PUBLICATIONS

CNIPA, Notification of First Office Action for Chinese application CN202510025810.0, Feb. 17, 2025.

(Continued)

*Primary Examiner* — Anna K Kinsaul
(74) *Attorney, Agent, or Firm* — Hemisphere Law, PLLC

(57) ABSTRACT

The present disclosure provides a fully automated filling line for tissue culture flasks and a control method therefor. The line covers stations for material loading, flask loading, flask sorting, flask righting, degreasing, cleaning, filling, cap screwing, material unloading, transferring, sterilization, etc. Through the collaborative operation of a mechanical arm and a conveying line, an automatic processing flow of tissue culture flasks is achieved. The flask righting station accurately detects and processes a fallen flask through an image recognition algorithm. A visual detection mechanism includes steps of image collection, preprocessing, and feature extraction and matching, where camera parameters are optimized according to a conveying speed and a light intensity, image quality is improved through a composite filtering and correction algorithm, and a plurality of feature group vectors are extracted and input into a model to recognize a flask posture.

19 Claims, 4 Drawing Sheets

(51) Int. Cl.

| | |
|---|---|
| *B67C 3/00* | (2006.01) |
| *B67C 3/22* | (2006.01) |
| *B67C 3/24* | (2006.01) |
| *B67C 3/26* | (2006.01) |
| *B67C 7/00* | (2006.01) |

(52) U.S. Cl.

CPC .............. *B65B 57/02* (2013.01); *B65B 57/04* (2013.01); *B67C 3/007* (2013.01); *B67C 3/22* (2013.01); *B67C 3/24* (2013.01); *B67C 3/26* (2013.01); *B67C 7/0026* (2013.01); *B67C 7/0073* (2013.01); *B67C 7/008* (2013.01)

(58) Field of Classification Search

CPC .... B67C 3/22; B67C 3/24; B67C 3/26; B67C 7/0026; B67C 7/0073; B67C 7/008; A01H 4/001

USPC ..................................... 53/425, 167, 53, 282

See application file for complete search history.

(56) References Cited

U.S. PATENT DOCUMENTS

| | | | | |
|---|---|---|---|---|
| 2011/0149065 | A1* | 6/2011 | Buchwald et al. .......................... | G01B 11/2433 |
| | | | | 348/127 |
| 2014/0196366 | A1* | 7/2014 | Teasdale ................ | A01G 9/088 |
| | | | | 414/226.01 |
| 2019/0071297 | A1* | 3/2019 | Hayakawa et al. ....... | B67C 3/00 |
| 2019/0178747 | A1 | 6/2019 | Bianchi et al. | |
| 2022/0371242 | A1 | 11/2022 | Gögülter | |
| 2022/0388833 | A1 | 12/2022 | Schmidt | |

OTHER PUBLICATIONS

CNIPA, Notification to grant patent right for Chinese application CN202510025810.0, Mar. 3, 2025.

\* cited by examiner

FULLY AUTOMATED FILLING LINE FOR TISSUE CULTURE FLASKS AND CONTROL METHOD THEREFOR

FIELD OF INVENTION

The present disclosure relates to the technical field of tissue culture flask cleaning, particularly to a fully automated filling line for tissue culture flasks and a control method therefor.

DESCRIPTION OF RELATED ARTS

In industrial tissue culture production of seedlings of traditional Chinese medicinal herbs from Orchidaceae Juss. and flowers, a large amount of tissue culture flasks are required. To reduce costs, glass tissue culture flasks are generally used, which can be reused after cleaning. We have applied the patent CN117502244A, which discloses a heating, cleaning, and filling line for tissue culture containers. It includes a material loading station, a preheating station, a degreasing station, a tissue culture container cleaning station, a screwing station and a sorting station that are sequentially arranged. A conveying chain is arranged between adjacent stations. One side of the screwing station is provided with a cap conveying station. Tissue culture flasks are heated at the preheating station, such that culture media at bottoms of the flasks are liquefied. This step reduces adhesion of the culture media, simplifies the cleaning process of the culture media in the tissue culture flasks, minimizes blockages of sewer pipes, and mitigates environmental pollution. Cleaning efficiency and degreasing rates are improved through scraping of residual culture media in the tissue culture flasks after liquefaction at the degreasing station. Instead of manual cleaning, a machine can remove solid culture media attached to interiors of the culture flasks without hydraulic cleaning. In addition, production of the tissue culture flasks can be directly completed through fine cleaning and a filling station. Thus, work efficiency is improved, and intensity of manual operation, waste of water resources, and environmental pollution are reduced.

However, the patent CN117502244A achieves full automation to a certain extent, but it still has some shortcomings in the degree of automation. Specifically, it is unable to deal with fallen flasks in a batch, which requires manual intervention in an early stage. Moreover, the tissue culture flasks fail to be automatically unloaded and transferred to a sterilization pot for sterilization.

Thus, there is an urgent need for a new fully automated filling line for tissue culture flasks and a control method therefor to solve existing technical problems.

SUMMARY OF THE PRESENT INVENTION

Examples of the present disclosure provide a fully automated filling line for tissue culture flasks and a control method therefor, so as to solve problems in the prior art, such as insufficient automation and inability to implement fallen flask processing.

A core technology of the present disclosure is mainly to upgrade and transform the original line, and implement more efficient fully automated filling of tissue culture flasks by providing an additional flask righting station and some additional apparatuses in combination with a new control method.

In a first aspect, the present disclosure provides a fully automated filling line for tissue culture flasks. The fully automated filling line includes:

a material loading and conveying line, configured to input to-be-cleaned tissue culture flask boxes, where each of the tissue culture flask boxes is filled with the tissue culture flask;

a flask loading station, arranged at one side of a tail end of the material loading and conveying line and provided with a flask loading mechanical arm having a working range covering the tail end of the material loading and conveying line and a flask sorting station, where the flask loading mechanical arm is configured to transfer the tissue culture flasks on the material loading and conveying line from the tissue culture flask boxes to the flask sorting station in batches;

the flask sorting station, provided with a flask sorting apparatus and configured to temporarily accommodate the tissue culture flasks and sequentially input the tissue culture flasks into a flask righting station;

the flask righting station, configured to detect the passing tissue culture flasks through an image recognition algorithm, mark the fallen tissue culture flask, and push the fallen tissue culture flask out through an execution component when the fallen tissue culture flask moves to a preset position;

a degreasing station, provided with a degreasing apparatus, where the degreasing apparatus is arranged at an output end of the flask righting station and configured to receive the detected tissue culture flasks and perform degreasing on them;

an external cleaning station, provided with an external cleaning apparatus, where the external cleaning apparatus is arranged at an output end of the degreasing apparatus and configured to receive the degreased tissue culture flasks and perform external cleaning on them;

an internal cleaning station, provided with an internal cleaning apparatus, where the internal cleaning apparatus is arranged at an output end of the external cleaning apparatus and configured to receive the externally cleaned tissue culture flasks and perform internal cleaning on them;

a filling station, provided with a filling apparatus, where the filling apparatus is arranged at an output end of the internal cleaning apparatus and configured to receive the internally cleaned tissue culture flasks and perform filling on them;

a cap screwing station, provided with a cap screwing apparatus, where the cap screwing apparatus is arranged at an output end of the filling apparatus and configured to receive the filled tissue culture flasks and perform cap placing and screwing on them;

a cap placing station, provided with a cap placing apparatus, where the cap placing apparatus is arranged at an input end of one side of the cap screwing apparatus and configured to provide caps for the tissue culture flasks;

a box loading and conveying line, connected to the material loading and conveying line and configured to convey the material boxes from which the tissue culture flasks have been taken on the material loading and conveying line to one side of a transferring station so as to be taken away;

a material unloading station, provided with a material unloading mechanical arm having a working range covering a tail end of the box loading and conveying line, the transferring station, and an output end of the cap placing apparatus, where the material unloading mechanical arm is configured to transfer the material boxes on the box loading and conveying line to the transferring station and transfer the tissue culture flasks after cap screwing in batches into a material box at the transferring station;

the transferring station, provided with an automatic guided vehicle (AGV), where the material boxes filled with the tissue culture flasks are transferred to a sterilization station through the AGV; and the sterilization station, provided with a sterilization pot configured to sterilize the tissue culture flasks.

Further, an additional flask righting station is arranged between the external cleaning station and the internal cleaning station.

Further, the material boxes on the AGV are stacked in one or more layers.

Further, the flask righting station includes a conveying track, a visual detection mechanism arranged above the conveying track, an execution component arranged at one side of the conveying track, and an output track cooperating with the execution component. The conveying track is provided with an opening in communication with an input opening at a top end of the output track. The execution component is arranged at an opposite side of the opening.

Further, a visual processing method carried by the visual detection mechanism specifically includes the following steps:

collecting an image;

preprocessing the collected image;

performing feature extraction and matching on the preprocessed image; and transmitting a matching result to the execution component.

Further, in the collecting an image of the visual processing method, camera parameters are optimized in real time through a speed of the conveying track and an ambient light intensity, a shutter speed is reduced in a same proportion if the speed of the conveying track increases, and an International Standardization Organization (ISO) value is increased and an aperture is enlarged accordingly if the ambient light intensity decreases.

In the preprocessing, filtering is performed through an adaptive composite filtering framework, followed by an adaptive gamma correction Retinex algorithm to enhance flask contour texture sharpness, improve background separation clarity, and thus boost visual quality and processing efficiency of the image.

Further, in the performing feature extraction and matching of the visual processing method, extracted features include shape features, texture features, and edge features. The shape features quantify flask regularity through measurement of a perimeter, an area, and circularity. The texture features evaluate surface texture complexity through computation of contrast, correlation, energy, and entropy using a gray level co-occurrence matrix. The edge features detect a flask posture through extraction of an edge contour using a Canny operator and fitting of a circle or a straight line using Hough transform. Then, the shape features, the texture features, and the edge features are combined to construct vectors representing the flask's position and posture.

The matching is performed by inputting the vectors representing the flask's position and posture into a trained model, and outputting the matching result through the model.

The trained model is trained by marking image samples of upright and fallen tissue culture flasks.

Further, in the performing feature extraction and matching of the visual processing method, a contour pixel point set of the tissue culture flasks is recognized through an image contour detection algorithm. A contour is tracked through a chain code method. Coding is performed according to a position relationship of adjacent pixel points. A perimeter value is obtained through accumulation of coding lengths.

Based on the pixel points of the contour, the area is computed through a Green formula or an integral method.

According to the perimeter and the area, the circularity is computed according to a circularity formula.

Further, in the performing feature extraction and matching of the visual processing method, the trained model is constructed and trained through a support vector machine or a convolutional neural network.

In a second aspect, the present disclosure provides a control method for a fully automated filling line for tissue culture flasks. The control method includes the following steps:

S00, inputting to-be-cleaned tissue culture flask boxes into a working range of a flask loading station through a material loading and conveying line, and transferring tissue culture flasks to a flask sorting apparatus at a flask sorting station in batches through a flask loading mechanical arm at the flask loading station; and conveying, after the tissue culture flasks are completely removed from material boxes of the tissue culture flask boxes, the material boxes to one side of a transferring station through a box loading and conveying line;

S10, sequentially inputting the tissue culture flasks into a flask righting station through the flask sorting apparatus; and transferring the material boxes on the box loading and conveying line to the transferring station through a material unloading mechanical arm at a material unloading station;

S20, detecting postures of the passing tissue culture flasks through the flask righting station, marking the fallen tissue culture flask, and pushing the fallen tissue culture flask out through an execution component when the fallen tissue culture flask moves to a preset position;

S30, performing degreasing on the tissue culture flasks detected as qualified through a degreasing apparatus at a degreasing station;

S40, performing external cleaning on the degreased tissue culture flasks through an external cleaning apparatus at an external cleaning station;

S50, performing internal cleaning on the externally cleaned tissue culture flasks through an internal cleaning apparatus at an internal cleaning station;

S60, performing filling on the internally cleaned tissue culture flasks through a filling apparatus at a filling station;

S70, performing cap placing and screwing on the filled tissue culture flasks through a cap screwing apparatus at a cap screwing station, with caps provided by the cap screwing apparatus through a cap placing apparatus at a cap placing station;

S80, transferring the tissue culture flasks after cap screwing to the material boxes at the transferring station in batches through the material unloading mechanical arm at the material unloading station; and S90, transferring the material boxes filled with the tissue culture flasks to a sterilization station through an AGV at the transferring station for sterilization.

The main contributions and innovations of the present disclosure are as follows:

1. High-efficiency automated processing is achieved. The present disclosure constructs a complete fully automated filling line for tissue culture flasks, which integrates entire-process stations such as material loading, cleaning, filling, cap screwing, material unloading, transferring, and sterilization. All the stations are closely cooperated and automatically connected without frequent manual intervention in the entire process from material loading to sterilization of the tissue culture flasks. Compared with the prior art, processing efficiency is greatly improved, and a processing cycle of the tissue culture flasks is shortened, strongly supporting the industrialized mass production requirements of seedlings, stabilizing consistent product quality, and reducing labor costs and human error rates.

2. A precise fallen flask processing mechanism is introduced. The flask righting station is arranged in an innovative manner, combining an advanced image recognition algorithm with an efficient execution component. The postures of the tissue culture flasks are monitored in real time, accurately recognizing the fallen flasks for automatic removal. In this way, interference of the fallen flasks in a production process is avoided, and smooth and stable operation of the line is ensured. This function, a missing link in the prior art, effectively enhances automation and reliability of production, reduces apparatus faults and product loss caused by the fallen flasks, and improves overall production efficiency and yield.

3. A visual detection process is optimized. The visual detection mechanism at the flask righting station intelligently optimizes the camera parameters according to the conveying speed and the ambient light intensity during image collection to ensure a clear image. Preprocessing is performed through an adaptive composite filtering and gamma correction Retinex algorithm, such that image quality is significantly improved; shape, texture, and edge features are accurately extracted to create flask position and posture vectors; and the postures of the flasks are accurately determined with the help of a precise training model. Compared with the prior art, detection accuracy and adaptability are significantly improved, which lays a solid foundation for accurate fallen flask processing, improves an intelligent level and production stability of the line, and achieves excellent performance in a complex production environment.

Details of one or more examples of the present disclosure are given in the following accompanying drawings and description to make other features, objectives, and advantages of the present disclosure more concise.

BRIEF DESCRIPTION OF THE DRAWINGS

The accompanying drawings, used to provide a further understanding of the present disclosure, constitute a part of the present disclosure, and illustrative examples of the present disclosure and their description serve to explain the present disclosure and are not to be construed as unduly limiting the present disclosure. In the drawings.

6

Figure 3:
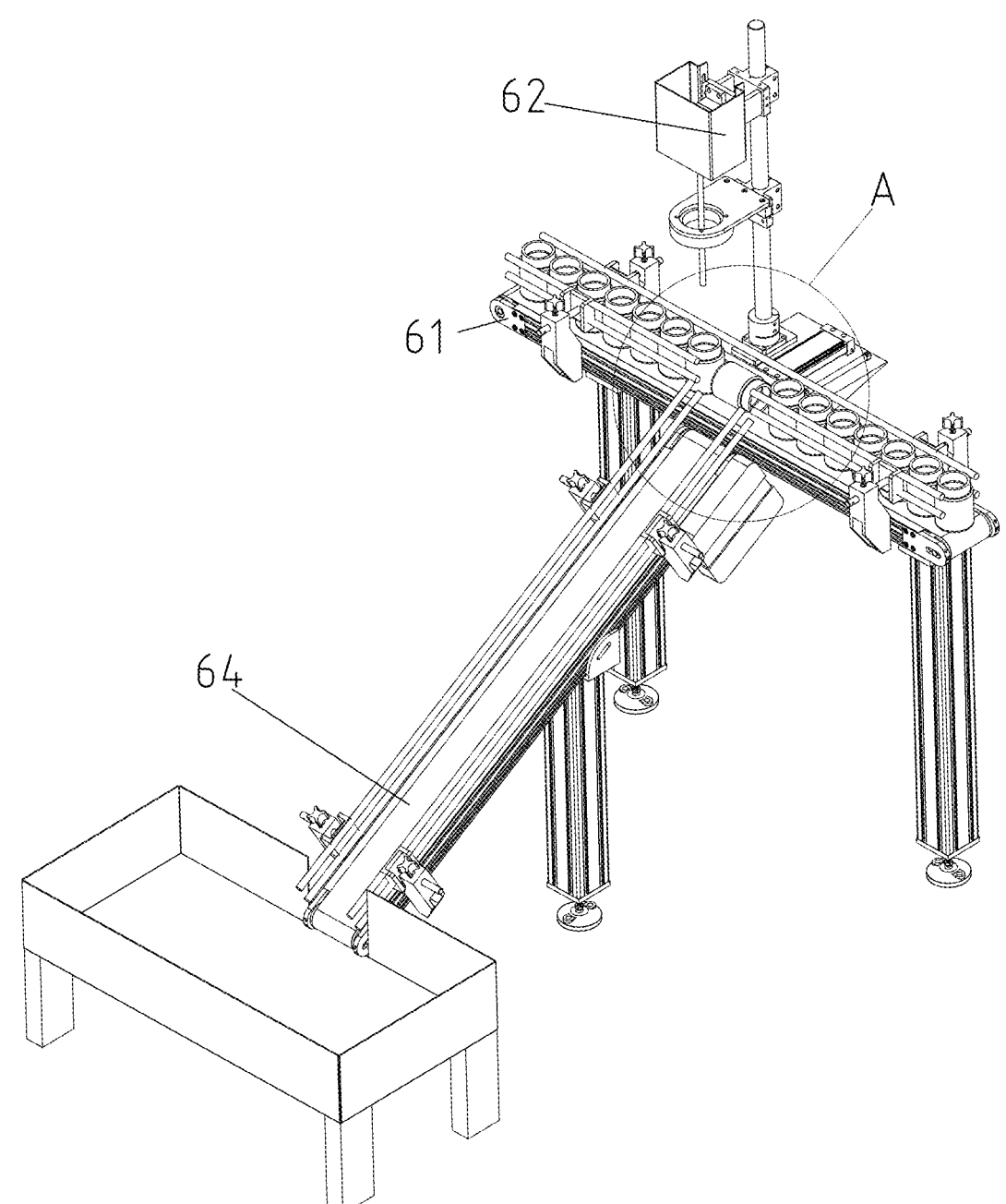
Figure 4:
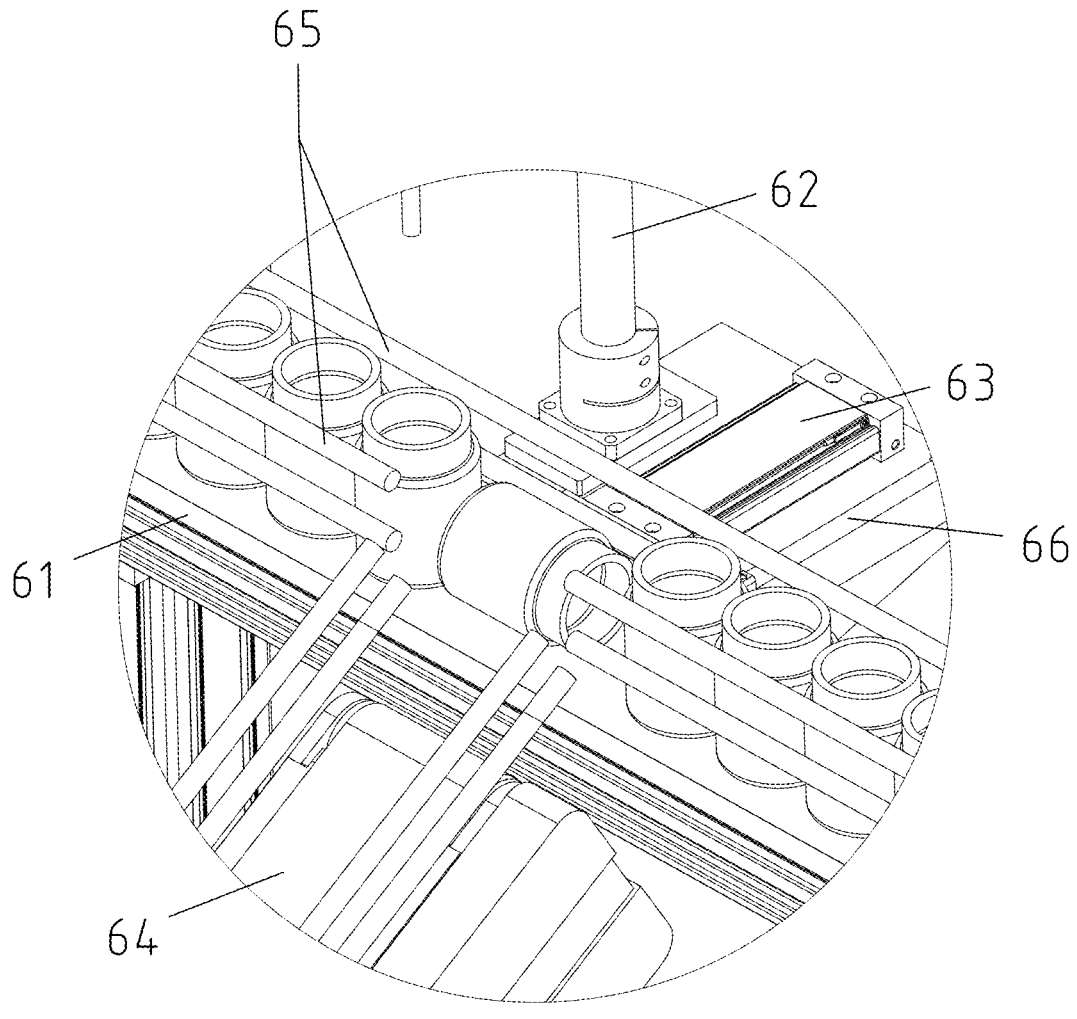

FIG. 3 is a perspective view of a flask righting station according to an example of the present disclosure; and FIG. 4 is an enlarged view of A in FIG. 3.

In the figures, 1, operator; 2, material loading and conveying line; 3, box loading and conveying line; 4, flask sorting station; 5, flask loading station; 6, flask righting station; 7, degreasing station; 8, external cleaning station; 9, internal cleaning station; 10, filling station; 11, cap placing station; 12, cap screwing station; 13, material unloading station; 14, transferring station; 15, sterilization station; 16, flask loading mechanical arm; 17, material unloading mechanical arm; 18, automatic guided vehicle (AGV); 61, conveying track; 62, visual detection mechanism; 63, execution component; 64, output track; 65, guide rod; 66, blocking and limiting air cylinder.

DETAILED DESCRIPTION OF THE PREFERRED EMBODIMENT

Illustrative examples will be described in detail herein and shown in the accompanying drawings illustratively. When the following description involves the accompanying drawings, unless otherwise specified, an identical reference number in different accompanying drawings denotes identical or similar elements. Embodiments described in the following illustrative examples do not denote all embodiments consistent with one or more examples of the present disclosure. On the contrary, the embodiments are merely instances of an apparatus and a method consistent with some aspects of one or more examples of the description as detailed in the appended claims.

It should be noted that in other examples, the steps of the corresponding method may not necessarily be executed in the order shown and described in the description. In some other examples, the method may include more or less steps than those described herein. In addition, a single step described in the description may be decomposed into a plurality of steps for description in other examples, and the steps described herein may be combined into a single step in other examples.

Example 1

The present disclosure aims to provide a fully automated filling line for tissue culture flasks. Specifically, with reference to FIG. 1, the fully automated filling line includes:

a material loading and conveying line 2, configured to input to-be-cleaned tissue culture flask boxes, where each of the tissue culture flask boxes includes a material box and a tissue culture flask placed in the material box;

a flask loading station 5, arranged at one side of a tail end of the material loading and conveying line 2, where the flask loading station 5 is provided with a flask loading mechanical arm 16 having a working range covering the tail end of the material loading and conveying line 2 and a flask sorting station 4, and the flask loading mechanical arm 16 is configured to transfer the tissue culture flasks on the material loading and conveying line 2 from the tissue culture flask boxes to the flask sorting station 4 in batches;

the flask sorting station 4, provided with a flask sorting apparatus and configured to temporarily accommodate the tissue culture flasks and sequentially input the tissue culture flasks into a flask righting station 6;

the flask righting station 6, configured to detect the passing tissue culture flasks through an image recognition algorithm, mark the fallen tissue culture flask, and push the fallen tissue culture flask out through an execution component 63 when the fallen tissue culture flask moves to a preset position;

a degreasing station 7, provided with a degreasing apparatus, where the degreasing apparatus is arranged at an output end of the flask righting station 6 and configured to receive the detected tissue culture flasks and perform degreasing on them;

an external cleaning station 8, provided with an external cleaning apparatus, where the external cleaning apparatus is arranged at an output end of the degreasing apparatus and configured to receive the degreased tissue culture flasks and perform external cleaning on them;

an internal cleaning station 9, provided with an internal cleaning apparatus, where the internal cleaning apparatus is arranged at an output end of the external cleaning apparatus and configured to receive the externally cleaned tissue culture flasks and perform internal cleaning on them;

a filling station 10, provided with a filling apparatus, where the filling apparatus is arranged at an output end of the internal cleaning apparatus and configured to receive the internally cleaned tissue culture flasks and perform filling on them;

a cap screwing station 12, provided with a cap screwing apparatus, where the cap screwing apparatus is arranged at an output end of the filling apparatus and configured to receive the filled tissue culture flasks and perform cap placing and screwing on them;

a cap placing station 11, provided with a cap placing apparatus, where the cap placing apparatus is arranged at an input end of one side of the cap screwing apparatus and configured to provide caps for the tissue culture flasks;

a box loading and conveying line 3, connected to the material loading and conveying line 2 and configured to convey the material boxes from which the tissue culture flasks have been taken on the material loading and conveying line 2 to one side of a transferring station 14 so as to be taken away;

a material unloading station 13, provided with a material unloading mechanical arm 17, where the material unloading mechanical arm 17 has a working range covering a tail end of the box loading and conveying line 3, the transferring station 14, and an output end of the cap placing apparatus, and the material unloading mechanical arm is configured to transfer the material boxes on the box loading and conveying line 3 to the transferring station 14 and transfer the tissue culture flasks after cap screwing in batches into the material boxes at the transferring station 14;

the transferring station 14, provided with an automatic guided vehicle (AGV) 18, where the material boxes filled with the tissue culture flasks are transferred to a sterilization station 15 through the AGV 18; and preferably, the material boxes on the AGV 18 are stacked in one or more layers to make full use of the AGV 18; and the sterilization station 15, provided with a sterilization pot configured to sterilize the tissue culture flasks.

The improvement of the present disclosure lies in the addition of the material loading and conveying line 2, the box loading and conveying line 3, the flask loading mechanical arm 16, the material unloading mechanical arm 17, the AGV 18, and the flask righting station 6. The apparatuses at the other stations are of the prior art, as described in patent CN117502244A or other undisclosed but applied patents, or these apparatuses may be other apparatuses that are disclosed in the market. Thus, structures and principles of the flask sorting apparatus, the degreasing apparatus, the external cleaning apparatus, the internal cleaning apparatus, the filling apparatus, the cap screwing apparatus, the cap placing apparatus and the sterilization pot will not be repeated herein. Similarly, the material loading and conveying line 2, the box loading and conveying line 3, the flask loading mechanical arm 16, the material unloading mechanical arm 17, and the AGV 18 are additional structures but existing commercially available products, so their structures and principles will not be repeated herein either.

Figure 1:
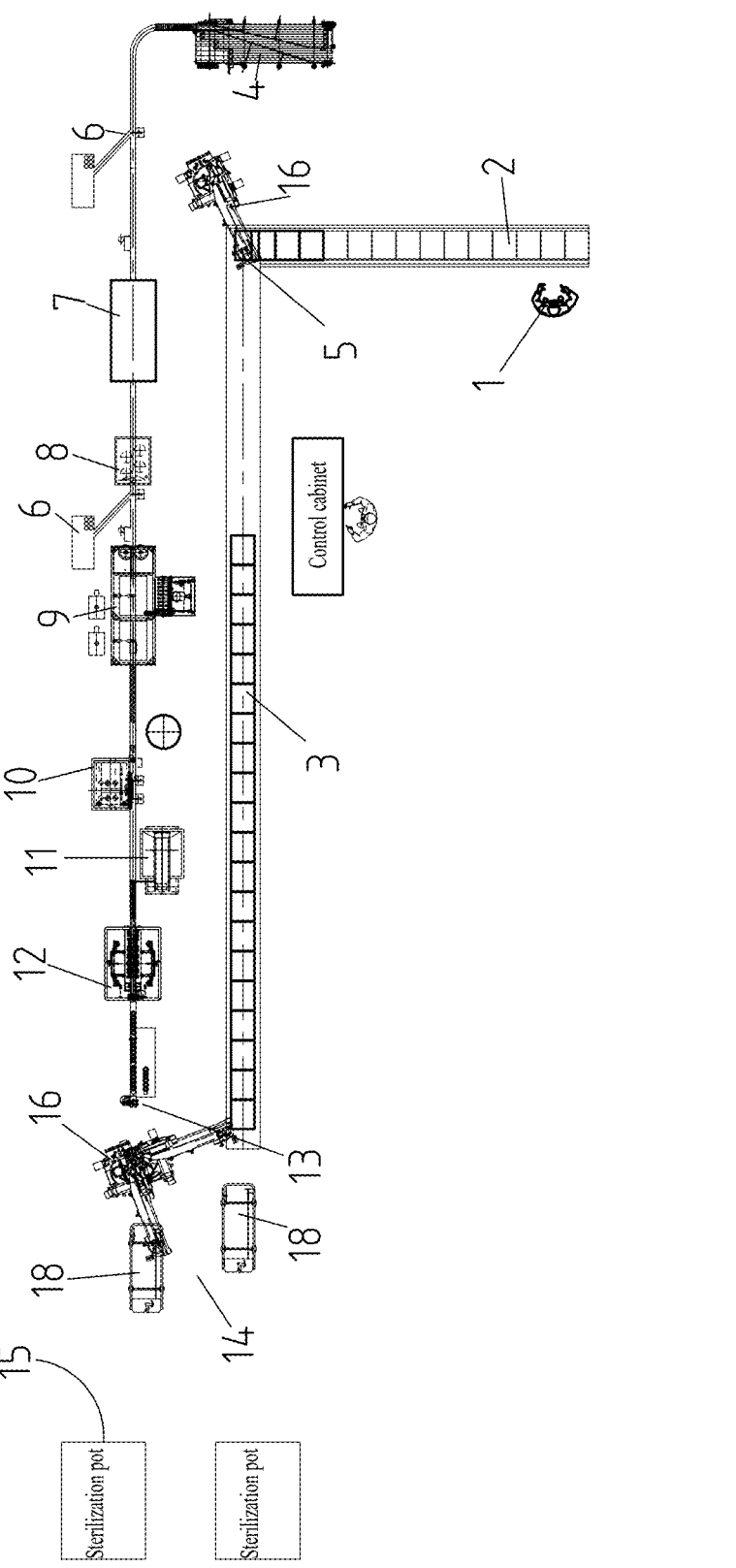
FIG. 1 is a top view of a fully automated filling line for tissue culture flasks according to an example of the present disclosure.
Figure 2:
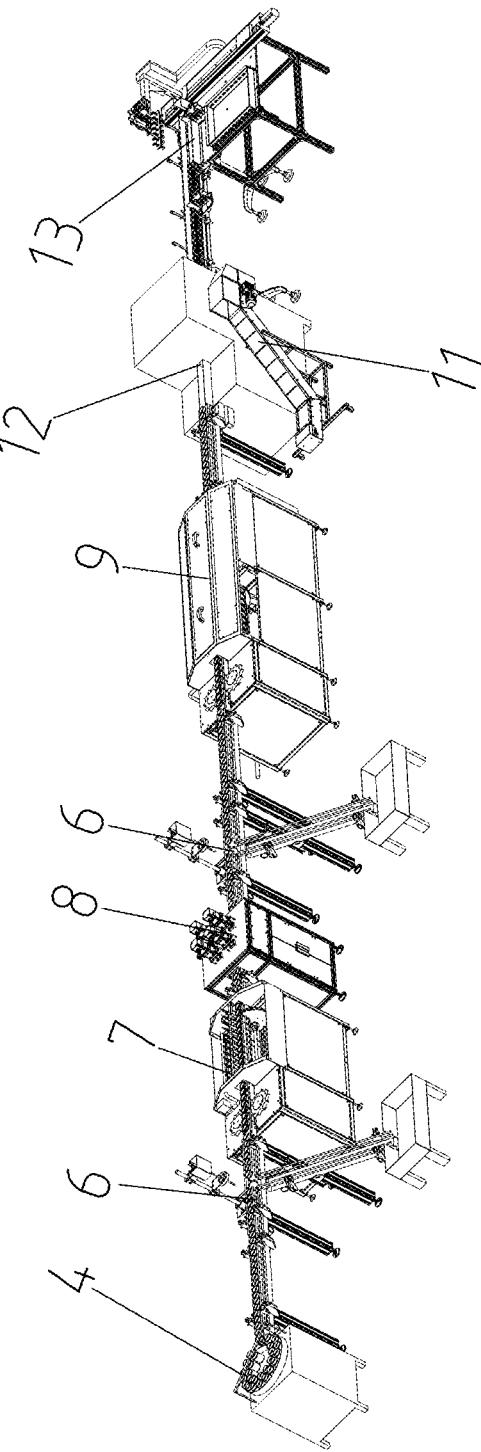
FIG. 2 is a structural schematic diagram of another embodiment of a fully automated filling line for tissue culture flasks according to an example of the present disclosure.

As shown in FIG. 2, if a filling operation is not needed, the filling station 10 may be directly removed, and cap placing and screwing may be directly performed after internal cleaning is completed. The apparatuses at the flask sorting station 4 in FIG. 1 and FIG. 2 are different yet have a consistent basic principle, both functioning to sequentially input the tissue culture flasks into the line. Principles and structures of these apparatuses will not be repeated herein, which belong to applications of the existing apparatuses.

In this example, as shown in FIG. 3 and FIG. 4, the flask righting station 6 includes a conveying track 61, a visual detection mechanism 62 arranged above the conveying track 61, an execution component 63 arranged at one side of the conveying track 61, and an output track 64 cooperating with the execution component 63. The conveying track 61 is provided with an opening in communication with an input opening at a top end of the output track 64. The execution component 63 is arranged at an opposite side of the opening. The conveying track 61 is provided with a guide rod 65 for guiding the tissue culture flasks, such that the execution component 63 may penetrate a gap to push the fallen tissue culture flasks out. Preferably, an air cylinder (flask pushing cylinder) or an electric cylinder may be used as the execution component 63 herein. The air cylinder is controlled by an electromagnetic valve. Or, the fallen tissue culture flasks may be blocked by adding a blocking and limiting air cylinder 66. One preferable solution is as follows:

Firstly, position and posture images of the tissue culture flasks in a normal state and the fallen tissue culture flasks are input into a recognition system in advance. Then, an industrial area-array camera is employed to capture real-time images of the tissue culture flasks as they pass along the conveying track 61, thereby detecting their current positions and postures. Upon detecting a fallen flask, a fallen flask signal is output to a control system, and the control system controls the blocking and limiting air cylinder 66 to extend out to block the fallen flask. After the blocking and limiting air cylinder 66 extends out in place, the control system controls the flask pushing cylinder to push the fallen tissue culture flask to the output track 64. Then, the flask pushing cylinder is controlled to retract, allowing the subsequent flasks to continue to move forward. Whether a next tissue culture flask is fallen is continuously recognized through the industrial area-array camera. If a position and a posture of the next tissue culture flask are normal, the control system controls the blocking and limiting air cylinder 66 to retract, and the subsequent tissue culture flasks continue to move forward smoothly. Input point positions of the specific control logic are shown in Table 1 below:

12,617,572 B2

9

TABLE 1

| Position | Point position |
| --- | --- |
| Visual recognition signal of a fallen flask state | X1 |
| Visual recognition signal of an upright flask state and a missing flask state | X2 |
| Flask pushing cylinder extension in-place sensor (magnetic switch) | X3 |
| Flask pushing cylinder retraction in-place sensor (magnetic switch) | X4 |
| Extension in-place sensor of the blocking and limiting air cylinder 66 | X5 |
| Retraction in-place sensor of the blocking and limiting air cylinder 66 | X6 |

Output point positions are shown in Table 2 below:

TABLE 2

| Position | Point position |
| --- | --- |
| Three-position five-way electromagnetic valve of the flask pushing cylinder | Y1 |
| Three-position five-way electromagnetic valve of the blocking and limiting air cylinder 66 | Y2 |
| Electric motor of the conveying track 61 | Y3 |
| Electric motor of the output track 64 | Y4 |

The control logic is as follows:

Step 1: A host computer controls the Y3 motor to rotate forward to drive the tissue culture flasks to move forward, and the industrial area-array camera photographs the positions and postures of the flasks on the conveying track 61 in real time. In this case, the X2 point position is always kept in a triggered state.

Step 2: When the X1 point position is triggered, it indicates the presence of a fallen flask on the conveying track 61. At this point, the host computer controls the electromagnetic valve Y2 to be powered on, the electromagnetic valve moves to control a piston of the blocking and limiting air cylinder 66 to extend, and the tissue culture flask is prevented from moving forward.

Step 3: When the X5 point position is triggered, it indicates that the blocking and limiting air cylinder 66 extends in place. At this point, the host computer controls the electromagnetic valve Y1 to be powered on, and a piston of the flask pushing cylinder extends to push the fallen tissue culture flask to the output track 64. Meanwhile, the host computer controls Y4 to be powered on to rotate forward, so as to drive the tissue culture flasks on the output track 64 into a collection box in real time.

Step 4: When the X3 point position is triggered, it indicates that the piston of the flask pushing cylinder extends in place, and the tissue culture flasks are transferred to the output track 64. Then, the host computer controls Y1 to be powered off, the electromagnetic valve is reset, and the piston of the flask pushing cylinder retracts.

Step 5: When the X4 point position is triggered, it indicates that the flask pushing cylinder retracts in place. At this point, the industrial area-array camera continues to detect states of the tissue culture flasks on the conveying track 61. When the X1 point position is not triggered and the X2 point position is triggered, the host computer controls the electromagnetic valve Y2 to be powered off, the electromagnetic valve is reset, and the piston of the blocking and limiting air cylinder 66 retracts. When the X6 point position is triggered, the blocking and limiting air cylinder 66 retracts in place, and the conveying track 61 may pass smoothly.

Step 6: Steps 1 to 5 are repeated to detect whether a fallen flask appears on the conveying track 61 in real time, and perform accurate removal.

In this example, a visual processing method specifically includes the following steps:

Step 1, an image is collected.

As a core collection apparatus, the industrial area-array camera's resolution, frame rate, and field of view are accurately determined according to dimensions of the tissue culture flasks and a speed of the conveying track 61. For instance, when a diameter of the tissue culture flasks is 80 mm and the speed of the conveying track 61 is 0.5 m/s, a camera having a resolution of 2048×1536 pixels, a frame rate of 30 fps, and a field of view covering the conveying track 61 by a width of 300 mm is selected to ensure clear capture of the flasks' details and motion trajectory without any smearing and blurring. The camera is mounted 400 mm above the conveying track 61, with its optical axis perpendicular to the conveying track 61, and the collected image transmitted to an image processing unit.

Preferably, camera parameters may be dynamically adjusted according to the speed of the conveying track 61 and an ambient light intensity.

Key nodes of the line are provided with light intensity and speed sensors to monitor parameters in real time (accuracy: ±2%) and transmit such data to the control system of the camera. According to a speed change (±10%), a shutter speed is dynamically adjusted through a proportion integration differentiation (PID) controller. If the speed increases by 10%, the shutter speed is reduced from $\frac{1}{500}$ second to $\frac{1}{1,100}$ second, ensuring that movement of flask bodies is frozen and the image is clear and sharp. When the light intensity fluctuates (±300 lux), a fuzzy logic controller coordinates an International Standardization Organization (ISO) value and an aperture. For instance, the light intensity drops by 300 lux, the ISO rises from 800 to 2,000, and the aperture is expanded from f/2.8 to f/4.5. Thus, it is ensured that the image is properly exposed and the details are complete, laying the groundwork for subsequent accurate detection.

Step 2, the collected image is preprocessed.

The collected image is subjected to graying, filtering and noise reduction, and contrast enhancement in the image processing unit. Graying is performed through a weighted mean method. According to sensitivity of human eyes to RGB components (e.g., R: 0.299, G: 0.587, B: 0.114), a weight is given to transfer a gray image, and a data volume is reduced. Median filtering is employed to remove salt and pepper noise by scanning the image through a 3×3 template and sorting pixel values to replace a central pixel with a median value. Histogram equalization is used to enhance contrast by stretching distribution of gray values, such that a difference between a flask contour and a background is highlighted, and a foundation is laid for subsequent feature extraction.

Preferably, an adaptive composite filtering framework can also be adopted: after the salt and pepper noise is primarily removed through median filtering, wavelet threshold denoising is performed in a hierarchical manner according to noise levels, a high-frequency sub-band is shrunk by a soft threshold for noise reduction, and a low-frequency sub-band is enhanced by edge preservation. For weak noise, weighting is performed on bilateral filtering according to a pixel gray level and a spatial distance, ensuring fine noise removal while preserving edge textures. This multi-algorithm collaboration provides a stable image environment for feature extraction.

Preferably, an advanced Retinex enhancement algorithm may be utilized: an adaptive gamma correction Retinex (AGCWR) algorithm is introduced, parameters are adaptively adjusted according to local and global contrast of the image, an illumination component is weighted through a central surround function, and a reflection component is dynamically stretched to enhance contrast of details and suppress halo artifact. Such introduction can enhance flask contour texture sharpness, improve background separation clarity, and thus boost visual quality and processing efficiency of the image.

Step 3, feature extraction and matching are performed on the preprocessed image.

Features such as shapes, textures, and edges are extracted from the processed image. The shape features quantify flask regularity through computation of a perimeter, an area, and circularity ($4\pi\times$area/perimeter$^2$). The texture features evaluate surface texture complexity through computation of contrast, correlation, energy, and entropy using a gray level co-occurrence matrix. The edge features determine a posture through parameters of a straight-line section of a flask contour located by fitting of a straight line using Hough transform, where the flask contour is detected by a Canny operator. A plurality of features are combined to construct vectors representing the flask's position and posture, such as [circularity, contrast, edge straight-line slope 1, edge straight-line slope 2, . . . ].

Model training is implemented as follows: a large number of images of upright and fallen tissue culture flasks are marked, and are divided into training and test sets (with a 7:3 ratio). Classification models such as a support vector machine (SVM) and a convolutional neural network (CNN) are selected. For the SVM, a radial basis function kernel is selected according to feature vectors, and penalty parameters and kernel coefficients are adjusted to achieve high classification accuracy. For the CNN, a framework including convolution, pooling, and full connection layers is constructed, such as 3 convolution layers (convolution kernels 3×3, 5×5, 3×3), 2 pooling layers (a 2×2 window), and 2 full connection layers. A back propagation algorithm is used for training and optimization. An optimal model is selected and stored in a recognition system through test set verification. Camera image vectors are received in real time and input to determine the flask's position and posture, and the processed features may be input into the model to obtain a matching result.

Shape extraction and processing are as follows:

Perimeter C computation is performed as follows: an image contour detection algorithm (for instance, the find Contours function from the OpenCV library) is used for recognizing a contour pixel point set of the tissue culture flasks. A contour is tracked through a chain code method or Freeman chain codes. Coding is performed according to a position relationship of adjacent pixel points. A perimeter value is obtained through accumulation of coding lengths. For instance, if the pixel points of the contour are coded as 0 (horizontally rightward shift), 1 (upward-rightward oblique shift), 2 (perpendicularly upward shift), etc., sequentially. A total length of the chain codes, that is, the perimeter, is computed through contour traversing. This value is conducive to evaluation of regularity of flask shapes and distinguishing between flasks having different specifications.

Area S measurement is performed as follows: based on the pixel points of the contour, the area is computed through a Green formula or an integral method. A zone defined by the contour is divided into a plurality of small triangles or trapezoids, and an occupied pixel area of the flasks in the image is obtained through computation and accumulation of areas of all sub-zones. The Green formula transforms area computation into a line integral along the contour in a two-dimensional plane, improving computation efficiency and accuracy and providing basic data for determining a flask posture, as, flask falling may lead to change of area projection.

Circularity derivation is performed as follows: computation is performed through a formula, circularity=$4\pi S/C^2$, according to the perimeter C and the area S. Circularity close to 1 indicates that a shape of a flask is close to a standard circle. Circularity deviated from 1 indicates an irregular shape or an abnormal posture. This value sets a threshold benchmark for subsequent posture determination. Circularity less than 0.9 may indicate that the flask is tilted or fallen, which triggers further detection and confirmation.

A method for extracting and processing the texture features is as follows:

The gray level co-occurrence matrix is constructed as follows: a specific direction (for instance, horizontal, perpendicular, 45°, and 135°) and a displacement distance (set to 1 to 5 pixels according to a flask texture scale) are selected, co-occurrence frequency of pixel gray level values in the image is counted for the selected direction and distance, and a square matrix is constructed. With a horizontally rightward shift by 1 pixel as an instance, image pixels are traversed, and the number of occurrences of a pixel having a gray level value of j at a 1-pixel shift to the right side of a pixel with a gray level value of i is recorded in a matrix G(i,j). The matrix reflects spatial distribution and variation characteristics of texture gray levels.

Feature parameters are computed as follows: parameters such as the contrast, the correlation, the energy, and the entropy are computed from the gray level co-occurrence matrix. The contrast measures changes of image clarity and texture depths. The formula is as follows:

$$\sum_{i,j}|i-j|^2 G(i,j).$$

The correlation represents a linear relationship of a pixel gray level. The formula is as follows:

$$\sum_{i,j}\frac{(i-\mu_i)(j-\mu_j)G(i,j)}{\sqrt{\sigma_i^2\sigma_j^2}}$$

($\mu_i$ denotes a mean value of rows, and $$\sigma_i^2$$

denotes variance).

The energy reflects uniformity and thickness of textures. The formula is as follows:

$$\sum_{i,j}G(i,j)^2.$$

The entropy measures randomness and information content of textures. The formula is as follows:

$$-\sum_{i,j} G(i,\, j)\log G(i,\, j).$$

All the parameters describe texture characteristics of a flask surface cooperatively, so as to be conducive to distinguishing between upright flasks and fallen flasks (for instance, stretching deformation of the textures caused by flask falling changes the parameters) and addition of a multi-dimensional basis to posture determination.

A method for extracting and processing the edge features is as follows:

Canny operator edge detection is performed as follows: a Gaussian filter is used for smoothing the image for noise reduction, and high and low thresholds are set according to a gray level difference between the tissue culture flask and the background (for instance, when the background is uniform and low in gray level and the flasks are high in gray level, the low threshold is 50, and the high threshold is 150). The Canny operator detects edge points, and the edge points are connected to form the contour through a double threshold hysteresis method. Firstly, strong edge pixels are located according to the high threshold, and weak edges are connected to supplement the contour through low threshold pixels in a neighborhood. In this way, an edge pixel set of the contour of the flask is accurately located, a false edge caused by noise is suppressed, and clear edge information is provided for subsequent analysis.

Straight-line fitting by Hough transform is performed as follows: a coordinate space of edge pixel points is mapped to a parameter space (which is $(\rho, \theta)$ in polar coordinates), and voting is performed to count intersection points so as to determine straight-line parameters. If a horizontal straight line corresponds to $\theta=0°$ or $180°$ and different p value point sets in the parameter space, if a threshold is exceeded through voting, it is determined that there is a straight line, and the parameters such as slope and nodal increment are obtained through fitting of the straight-line section of the flask contour. The flask posture is analyzed through a multi-linear parameter combination. If a plurality of straight lines have similar slope and are distributed horizontally or perpendicularly, it indicates a high likelihood that the flask is upright, while abnormal slope or random distribution indicates a posture change. This approach provides key geometric clues for position and posture detection, enabling accurate determination of a flask state.

Step 4, a matching result is transmitted to the execution component 63.

If the execution component 63 obtains results of a fallen state, and the fallen tissue culture flasks are pushed out of the conveying track 61. For an upright state, no action is taken.

Example 2

Based on the same concept, the present disclosure further provides a control method for a fully automated filling line for tissue culture flasks. The control method includes the following steps:

S00, to-be-cleaned tissue culture flask boxes are input into a working range of a flask loading station 5 through a material loading and conveying line 2, and tissue culture flasks are transferred to a flask sorting apparatus at a flask sorting station 4 in batches through a flask loading mechanical arm 16 at the flask loading station 5; and after the tissue culture flasks are completely removed from material boxes of the tissue culture flask boxes, the material boxes are conveyed to one side of a transferring station 14 through a box loading and conveying line 3.

S10, the tissue culture flasks are sequentially input into a flask righting station 6 through the flask sorting apparatus; and the material boxes on the box loading and conveying line 3 are transferred to the transferring station 14 through a material unloading mechanical arm 17 at a material unloading station 13.

S20, postures of the passing tissue culture flasks are detected through the flask righting station 6, the fallen tissue culture flask is marked and then pushed out through an execution component 63 when the fallen tissue culture flask moves to a preset position.

S30, degreasing is performed on the tissue culture flasks detected as qualified through a degreasing apparatus at a degreasing station 7.

S40, external cleaning is performed on the degreased tissue culture flasks through an external cleaning apparatus at an external cleaning station 8.

S50, internal cleaning is performed on the externally cleaned tissue culture flasks through an internal cleaning apparatus at an internal cleaning station 9.

S60, filling is performed on the internally cleaned tissue culture flasks through a filling apparatus at a filling station 10.

S70, cap placing and screwing are performed on the filled tissue culture flasks through a cap screwing apparatus at a cap screwing station 12, with caps provided by the cap screwing apparatus through a cap placing apparatus at a cap placing station 11.

S80, the tissue culture flasks after cap screwing are transferred to the material boxes at the transferring station 14 in batches through the material unloading mechanical arm 17 at the material unloading station 13.

S90, the material boxes filled with the tissue culture flasks are transferred to a sterilization station 15 through an AGV 18 at the transferring station 14 for sterilization.

Preferably, an overall flow of the line is demonstrated as follows:

Apparatus preparation and startup: In a workshop of a seedling factory, the apparatus at each station is arranged according to a layout of the present disclosure. The material loading and conveying line 2, the flask loading mechanical arm 16, the flask sorting station 4, the flask righting station 6 (including the visual detection and removal mechanism), the degreasing station 7, the external cleaning station 8, the internal cleaning station 9, the filling station 10, the cap screwing station 12, the cap placing station 11, the box loading and conveying line 3, the material unloading mechanical arm 17, the AGV 18, and the sterilization station 15 are all set up sequentially. Upon system startup, all apparatuses undergo a self-check and enter a standby mode once no errors are detected, all conveying lines run at a constant speed, the mechanical arms return to their original positions, and the visual detection system initializes and loads model parameters.

Material loading to flask sorting: An operator 1 places 10 material boxes loaded with 300 tissue culture flasks at a start end of the material loading and conveying line 2. The conveying line moves the flasks to the flask loading station 5 at a speed of 0.3 m/s. The flask loading mechanical arm 16 (with a working range accurately covering a tail end of the material loading and conveying line 2 and an entrance of the flask sorting station 4, and travel accuracy of ±2 mm)

follows a programmed path to grasp and place the 300 tissue culture flasks in an orderly manner onto a flask sorting channel of the flask sorting station 4 within 10 min. The flask sorting apparatus (with a flexible thumbwheel mechanism operating at a rotating speed of 10 r/min) sequentially guides the tissue culture flasks into a main conveying line of the flask righting station 6 at a constant rate, maintaining a flask spacing of 15 cm to ensure collision-free stacking.

A multi-station processing flow: Real-time monitoring is performed through the visual detection system at the flask righting station 6 (provided with an industrial area-array camera having a resolution of 1920×1080, a frame rate of 25 fps, and a field of view covering the conveying line by a width of 250 mm). The flasks detected as qualified pass smoothly. After reception, the degreasing station 7 (provided with 4 groups of ultrasonic transducers with frequency of 40 kHz and power of 200 W) performs degreasing for 6 min through ultrasonic cavitation. The external cleaning station 8 (with 4 groups of brushes at a rotating speed of 120 r/min) cleans external walls of the flasks with brushes for 5 min. The internal cleaning station 9 (with 8 groups of brushes, cylinder thrust of 50 N, and a feeding speed of 5 mm/s) cleans internal walls of the flasks for 8 min. The filling station 10 (provided with a vacuum pump having a pumping speed of 10 L/min, and a sensor having timing accuracy ±0.1 s) completes filling according to a set volume of 100 ml and accuracy of 5 min. The cap screwing station 12 (provided with left and right belts having a rotating speed of 60 r/min) cooperates with the cap placing station 11 (provided with a flask cap channel having vibration frequency of 30 Hz) to complete cap screwing within 4 min.

Material loading, transferring and sterilization: After cap screwing, the flasks are moved to the material boxes at the transferring station 14 within 7 min through the material unloading mechanical arm 17 (with loading capacity of 10 kg and repeated positioning accuracy of ±1 mm). The transferring AGV 18 (with a load of 500 kg and navigation accuracy of ±10 mm) transfers the fully loaded boxes (each loaded with 30 flasks stacked in 3 layers) to the sterilization station 15 (provided with a sterilization pot having a heating rate of 5° C./min, and maintaining a temperature of 121° C. for a 20-min sterilization period cycle) within 12 min for sterilization along a planned path. At this point, a complete cycle of the line is completed, with all links in the entire process closely connected and operating stably and efficiently, such that solid automated support is provided for tissue culture flask processing.

Example 3

This example provides a scene analysis solution for fallen flask processing. The solution includes:

Fallen flask detection and response: In production, tissue culture flasks travel on a conveying line from internal cleaning to filling. At a certain moment, a flask falls over due to collision between the flasks. The visual detection system captures an image instantly (with acquisition exposure time of $\frac{1}{120}$ s and a gain of 1.5). After processing (0.2 s: graying, 3×3 median filtering, and histogram equalization), the image is matched with a pre-stored fallen flask position and posture template (fallen flasks are determined through a circularity threshold of 0.8), and a fallen flask signal (the X1 point position) is triggered. The control system responds within 0.5 s, drives the blocking and limiting air cylinder 66 (with a cylinder diameter of 32 mm, travel of 100 mm, and response time of 0.3 s) to extend out, and blocks the flask in place within 2 s. Meanwhile, the electric motor of the conveying line is slowed down by 20% to prevent subsequent flask accumulation.

Fallen flask removal: When the flask is blocked in place, the X5 point position is triggered. The control system enables the electromagnetic valve of the flask pushing cylinder (with a cylinder diameter of 25 mm, travel of 80 mm, and thrust of 40 N) to be powered on, and the pushing cylinder extends out in 0.4 s. The fallen flask is pushed to the fallen flask conveying line (with a bandwidth of 80 mm and a belt speed of 0.3 m/s) at a speed of 0.2 m/s. When the flask is pushed in place, the X3 point position is triggered, the electromagnetic valve of the pushing cylinder is powered off, and the cylinder retracts in 0.3 s. The electric motor of the fallen flask conveying line rotates forward for 5 s and conveys the flasks into a collection box (with a capacity of 20 flasks). During this process, the industrial area-array camera performs continuous monitoring. If a new flask is in a normal position and posture, the X2 point position continues to be triggered. When the X6 point position indicates that the blocking cylinder retracts in place (in 0.4 s), the electric motor of the conveying line restores to its original speed. In this way, fluency and continuity of the line are ensured, and interference and loss caused by the fallen flasks are reduced.

Example 4

This example provides a solution for visual detection optimization. The solution includes:

A dynamic parameter adjustment mechanism: In the afternoon, the light intensity of the workshop gradually decreases (from 1,000 lux to 600 lux) and the speeds of the conveying lines are slightly adjusted (from 0.3 m/s to 0.4 m/s). The visual detection system performs intelligent response, and camera parameters are optimized in real time. When the light intensity decreases, the ISO value linearly increases from 100 to 200, the aperture is expanded from F5.6 to F4, and the shutter speed is adjusted from $\frac{1}{120}$ s to $\frac{1}{150}$ s. As the speeds of the conveying lines increase, the camera frame rate is adaptively increased to 30 fps, the exposure time is reduced to $\frac{1}{180}$ s, and the gain is adjusted to 1.8. In this way, stable image quality (with a definition deviation within ±5% and mean brightness fluctuation within ±10%) is ensured, a reliable image source is provided for accurate detection, and adaptability of the system environment is improved.

Feature extraction and model determination efficiency: With an image in which a batch of tissue culture flasks are internally cleaned as an instance, after an optimized visual processing flow, the following features are extracted. A mean perimeter of 250 mm, an area of 5,000 mm$^2$, and circularity of 0.95 of the flasks are extracted as shape features. Texture features (with contrast 120, correlation 0.6, energy 0.3, and entropy 1.8) accurately reflect texture characteristics of scratches on the internal wall. Edge features are obtained by extraction of the contours using the Canny operator (high and low thresholds of 80 and 150) and fitting of straight lines with a slope deviation within ±5° using Hough transform. These features are combined to construct vectors and then input into a convolutional neural network model (with 5,000 training samples and an accuracy rate of 98%). Upright flasks are determined accurately (with a confidence rate of 99%) and directly proceed to the next station, and fallen flasks (circularity of 0.7 and texture entropy of 2.2 indicate an abnormal state) that occasionally appear are recognized and processed accurately. Thus, highprecision visual detection may ensure that the line produces high-quality tissue culture flasks efficiently.

Example 5

This example provides a preferable solution for feature extraction and matching. Specifically, 1) Fine Shape Feature Expansion An improved Fourier descriptor cooperates with ellipse fitting. Sampling is performed on discrete points of the contours of the tissue culture flasks. A Fourier descriptor algorithm is improved, selecting first 30 order coefficients according to curvature weighting of the contours, such that details (flask neck radians, flask curve changes) and an overall ellipse trend (an axis length, eccentricity) are depicted. The ellipse fitting is performed using a least square method, and the derived parameters facilitate location of directions and postures of the flasks. The two methods are combined to accurately construct a shape feature model, for instance, to distinguish between normal flasks and those with slight deformations, achieving a false determination rate of less than 1%.

Shape context feature embedding is implemented. Contour points are traversed, a sector-shaped neighborhood is drawn with a point as a center, distribution features of points in the neighborhood are counted to present as a histogram (with 8 directions and 5 distance intervals), and normalization is performed to obtain shape context feature vectors. In this way, a local structural relationship is captured, supplementing global description limitations of the Fourier descriptor. For instance, types of concave or convex positions of the flask bodies can be distinguished, discriminant dimensions of the shape features can be enhanced, and classification reliability can be improved.

2) Depth Texture Feature Mining

Two-dimensional Gabor and a three-dimensional local binary pattern (3DLBP) are fused to create a texture tensor. Two-dimensional Gabor filtering (with a scale of 4 to 8, a direction 0° to 180°, and an interval 30°) responds to flask textures in a multi-scale and multi-direction manner. The 3DLBP analyzes texture depth changes from a three-dimensional perspective (with a neighborhood 3×3×3, and a sampling radius 1.5). Response values of the two-dimensional Gabor and the 3DLBP are fused to generate a texture feature tensor, which represents a variation law of thickness, direction and depth of flask wall texture in three dimensions. For instance, abnormal textures caused by scratches and stains in the flasks can be accurately recognized, improving defect detection accuracy by 20%.

Wavelet transform is performed to analyze a texture hierarchy. Discrete wavelet transform (Daubechies4 wavelet base) decomposes a texture image frequency domain to obtain low-frequency approximation and high-frequency detail coefficients. According to a weighted coefficient of energy distribution, a hierarchical feature vector is constructed to describe multi-resolution characteristics of textures, and surface characteristics of the flasks are completely deconstructed from macro contours to micro defects. Thus, a rich texture basis is provided for classification.

3) Enhanced Deep Learning Feature Extraction

Innovation and optimization of a deep convolutional neural network (DCNN) framework are performed. Group convolution is implemented based on channels to reduce an amount of computation and parameter redundancy and improve feature extraction efficiency. Mixed pooling (a combination of maximum pooling and mean pooling) ensures that a feature map is rich in information. For instance, after improvement in a ResNet-50 framework, a training speed of a model increases by 40%, feature abstraction is strong, and key semantic features are extracted more accurately.

Multi-scale feature fusion and training reinforcement are performed. A feature pyramid network integrates bottom details and high-level semantics, enhancing context perception and assisting the model in locating and recognizing complex scene features of the flasks. Transfer learning is initialized with ImageNet pre-training weights to accelerate convergence and improve generalization. Generator-discriminator confrontation is constructed through confrontation training, and diverse samples are created, increasing robustness of the model against interferences such as illumination and flask wear, ensuring stability of feature determination, and reducing a false determination rate by 30%.

4) Robust and Accurate Multi-Modal Feature Matching and Decision-Making Process

A double-layer cascade classification architecture runs efficiently. Features of shapes, textures and deep learning are fused to generate high-dimensional multi-modal vectors which are input to a first-layer Adaboost classifier. Weak classifiers are trained to be integrated into a strong classifier according to the importance of the features, screening out key features to reduce dimensionality, shortening a computation space, and increasing speed by 30%. A sub-layer SVM uses a radial basis function and optimizes its parameters through grid search (C: 0.1 to 10, $\gamma$: 0.01 to 1) for accurate classification. A plurality of classifiers cooperate to optimize a classification boundary, such that a false determination rate is reduced while a recall rate is improved, and overall detection accuracy reaches 99.5% or above.

Intelligent control of a dynamic confidence threshold is performed. Bayesian decision-making theory computes a confidence threshold according to a false determination loss function (missing determination loss is set as 3 and false determination loss is set as 1) and a sample posterior probability. If the false determination rate exceeds 3%, the threshold is reduced by 5% to enhance sensitivity to anomaly capture. Conversely, if a correct determination rate is high (>98% for 100 consecutive samples), the threshold is increased by 3% to narrow a determination interval, balancing detection accuracy and efficiency. Real-time monitoring of sample distribution and model performance is carried out to dynamically adjust the threshold, achieving adaptive optimization, increasing detection efficiency by 60%, and ensuring efficient and accurate production.

Those skilled in the art should understand that all technical features of the examples can be arbitrarily combined. To simplify description, all possible combinations of all the technical features of the examples are not described. However, if only the combinations of these technical features do not conflict, they should be considered to be within the scope of the description.

The examples are merely several embodiments of the present disclosure. Although their description is relatively specific and detailed, they should not be construed as limiting the scope of the present disclosure. It should be noted that those of ordinary skill in the art can make various modifications and improvements on the premise of not deviating from the concept of the present disclosure, and these modifications and improvements fall within the protection scope of the present disclosure. Hence, the protection scope of the present disclosure should be subject to the appended claims.

The invention claimed is:

1. A fully automated filling line for tissue culture flasks, comprising:

a material loading and conveying line, configured to input to-be-cleaned tissue culture flask boxes, wherein each of the tissue culture flask boxes comprises a material box and a tissue culture flask placed in the material box;

a flask loading station, arranged at one side of a tail end of the material loading and conveying line and provided with a flask loading mechanical arm having a working range covering the tail end of the loading and conveying line and a flask sorting station, wherein the flask loading mechanical arm is configured to transfer the tissue culture flasks on the material loading and conveying line from the tissue culture flask boxes to the flask sorting station in batches;

the flask sorting station, provided with a flask sorting apparatus and configured to temporarily accommodate the tissue culture flasks and sequentially input the tissue culture flasks into a flask righting station;

the flask righting station, configured to detect the passing tissue culture flasks through an image recognition algorithm, mark the fallen tissue culture flask, and push the fallen tissue culture flask out through an execution component when the fallen tissue culture flask moves to a preset position;

a degreasing station, provided with a degreasing apparatus, wherein the degreasing apparatus is arranged at an output end of the flask righting station and configured to receive the detected tissue culture flasks and perform degreasing on them;

an external cleaning station, provided with an external cleaning apparatus, wherein the external cleaning apparatus is arranged at an output end of the degreasing apparatus and configured to receive the degreased tissue culture flasks and perform external cleaning on them;

an internal cleaning station, provided with an internal cleaning apparatus, wherein the internal cleaning apparatus is arranged at an output end of the external cleaning apparatus and configured to receive the externally cleaned tissue culture flasks and perform internal cleaning on them;

a filling station, provided with a filling apparatus, wherein the filling apparatus is arranged at an output end of the internal cleaning apparatus and configured to receive the internally cleaned tissue culture flasks and perform filling on them;

a cap screwing station, provided with a cap screwing apparatus, wherein the cap screwing apparatus is arranged at an output end of the filling apparatus and configured to receive the filled tissue culture flasks and perform cap placing and screwing on them;

a cap placing station, provided with a cap placing apparatus, wherein the cap placing apparatus is arranged at an input end of one side of the cap screwing apparatus and configured to provide caps for the tissue culture flasks;

a box loading and conveying line, connected to the material loading and conveying line and configured to convey the material boxes from which the tissue culture flasks have been taken on the material loading and conveying line to one side of a transferring station so as to be taken away;

a material unloading station, provided with a material unloading mechanical arm having a working range covering a tail end of the box loading and conveying line, the transferring station, and an output end of the cap placing apparatus, wherein the material unloading mechanical arm is configured to transfer the material boxes on the box loading and conveying line to the transferring station and transfer the tissue culture flasks after cap screwing in batches into the material boxes at the transferring station;

the transferring station, provided with an automatic guided vehicle (AGV), wherein the material boxes filled with the tissue culture flasks are transferred to a sterilization station through the AGV; and the sterilization station, provided with a sterilization pot configured to sterilize the tissue culture flasks.

2. The fully automated filling line for tissue culture flasks according to claim 1, wherein an additional flask righting station is arranged between the external cleaning station and the internal cleaning station.

3. The fully automated filling line for tissue culture flasks according to claim 1, wherein the material boxes on the AGV are stacked in one or more layers.

4. The fully automated filling line for tissue culture flasks according to claim 1, wherein the flask righting station comprises a conveying track, a visual detection mechanism arranged above the conveying track, an execution component arranged at one side of the conveying track, and an output track cooperating with the execution component; and the conveying track is provided with an opening in communication with an input opening at a top end of the output track, and the execution component is arranged at an opposite side of the opening.

5. The fully automated filling line for tissue culture flasks according to claim 4, wherein a visual processing method carried by the visual detection mechanism specifically comprises the following steps:

collecting an image;

preprocessing the collected image;

performing feature extraction and matching on the preprocessed image; and transmitting a matching result to the execution component.

6. The fully automated filling line for tissue culture flasks according to claim 5, wherein in the collecting an image of the visual processing method, camera parameters are optimized in real time through a speed of the conveying track and an ambient light intensity, a shutter speed is reduced in a same proportion if the speed of the conveying track increases, and an International Standardization Organization (ISO) value is increased and an aperture is enlarged accordingly if the ambient light intensity decreases; and in the preprocessing, filtering is performed through an adaptive composite filtering framework, followed by an adaptive gamma correction Retinex algorithm to enhance flask contour texture sharpness, improve background separation clarity, and thus boost visual quality and processing efficiency of the image.

7. The fully automated filling line for tissue culture flasks according to claim 5, wherein in the performing feature extraction and matching of the visual processing method, extracted features comprise shape features, texture features, and edge features; the shape features quantify flask regularity through measurement of a perimeter, an area, and circularity, the texture features evaluate surface texture complexity through computation of contrast, correlation, energy, and entropy using a gray level co-occurrence matrix, the edge features detect a flask posture through extraction of an edge contour using a Canny operator and fitting of a circle or a straight line using Hough transform; and then the shape features, the texture features, and the edge features are combined to construct vectors representing the flask's position and posture; and the matching is performed by inputting the vectors representing the flask's position and posture into a trained model, and outputting the matching result through the model, wherein the trained model is trained by marking image samples of upright and fallen tissue culture flasks.

8. The fully automated filling line for tissue culture flasks according to claim 6, wherein in the performing feature extraction and matching of the visual processing method, extracted features comprise shape features, texture features, and edge features; the shape features quantify flask regularity through measurement of a perimeter, an area, and circularity, the texture features evaluate surface texture complexity through computation of contrast, correlation, energy, and entropy using a gray level co-occurrence matrix, the edge features detect a flask posture through extraction of an edge contour using a Canny operator and fitting of a circle or a straight line using Hough transform; and then the shape features, the texture features, and the edge features are combined to construct vectors representing the flask's position and posture; and the matching is performed by inputting the vectors representing the flask's position and posture into a trained model, and outputting the matching result through the model, wherein the trained model is trained by marking image samples of upright and fallen tissue culture flasks.

9. The fully automated filling line for tissue culture flasks according to claim 7, wherein in the performing feature extraction and matching of the visual processing method, a contour pixel point set of the tissue culture flasks is recognized through an image contour detection algorithm, a contour is tracked through a chain code method, coding is performed according to a position relationship of adjacent pixel points, and a perimeter value is obtained through accumulation of coding lengths;

based on the pixel points of the contour, the area is computed through a Green formula or an integral method; and according to the perimeter and the area, the circularity is computed according to a circularity formula.

10. The fully automated filling line for tissue culture flasks according to claim 7, wherein in the performing feature extraction and matching of the visual processing method, the trained model is constructed and trained through a support vector machine or a convolutional neural network.

11. A control method for the fully automated filling line for tissue culture flasks according to claim 1, comprising the following steps:

S00, inputting the to-be-cleaned tissue culture flask boxes into the working range of the flask loading station through the material loading and conveying line, and transferring the tissue culture flasks to the flask sorting apparatus at the flask sorting station in batches through the flask loading mechanical arm at the flask loading station; and conveying, after the tissue culture flasks are completely removed from the material boxes of the tissue culture flask boxes, the material boxes to one side of the transferring station through the box loading and conveying line;

S10, sequentially inputting the tissue culture flasks into the flask righting station through the flask sorting apparatus; and transferring the material boxes on the box loading and conveying line to the transferring station through the material unloading mechanical arm at the material unloading station;

S20, detecting postures of the passing tissue culture flasks through the flask righting station, marking the fallen tissue culture flask, and pushing the fallen tissue culture flask out through the execution component when the fallen tissue culture flask moves to the preset position;

S30, performing degreasing on the tissue culture flasks detected as qualified through the degreasing apparatus at the degreasing station;

S40, performing external cleaning on the degreased tissue culture flasks through the external cleaning apparatus at the external cleaning station;

S50, performing internal cleaning on the externally cleaned tissue culture flasks through the internal cleaning apparatus at the internal cleaning station;

S60, performing filling on the internally cleaned tissue culture flasks through the filling apparatus at the filling station;

S70, performing cap placing and screwing on the filled tissue culture flasks through the cap screwing apparatus at the cap screwing station, with caps provided by the cap screwing apparatus through the cap placing apparatus at the cap placing station;

S80, transferring the tissue culture flasks after cap screwing to the material boxes at the transferring station in batches through the material unloading mechanical arm at the material unloading station; and S90, transferring the material boxes filled with the tissue culture flasks to the sterilization station through the AGV at the transferring station for sterilization.

12. A control method for the fully automated filling line for tissue culture flasks according to claim 2, comprising the following steps:

S00, inputting the to-be-cleaned tissue culture flask boxes into the working range of the flask loading station through the material loading and conveying line, and transferring the tissue culture flasks to the flask sorting apparatus at the flask sorting station in batches through the flask loading mechanical arm at the flask loading station; and conveying, after the tissue culture flasks are completely removed from the material boxes of the tissue culture flask boxes, the material boxes to one side of the transferring station through the box loading and conveying line;

S10, sequentially inputting the tissue culture flasks into the flask righting station through the flask sorting apparatus; and transferring the material boxes on the box loading and conveying line to the transferring station through the material unloading mechanical arm at the material unloading station;

S20, detecting postures of the passing tissue culture flasks through the flask righting station, marking the fallen tissue culture flask, and pushing the fallen tissue culture flask out through the execution component when the fallen tissue culture flask moves to the preset position;

S30, performing degreasing on the tissue culture flasks detected as qualified through the degreasing apparatus at the degreasing station;

S40, performing external cleaning on the degreased tissue culture flasks through the external cleaning apparatus at the external cleaning station;

S50, performing internal cleaning on the externally cleaned tissue culture flasks through the internal cleaning apparatus at the internal cleaning station;

S60, performing filling on the internally cleaned tissue culture flasks through the filling apparatus at the filling station;

S70, performing cap placing and screwing on the filled tissue culture flasks through the cap screwing apparatus at the cap screwing station, with caps provided by the cap screwing apparatus through the cap placing apparatus at the cap placing station;

S80, transferring the tissue culture flasks after cap screwing to the material boxes at the transferring station in batches through the material unloading mechanical arm at the material unloading station; and S90, transferring the material boxes filled with the tissue culture flasks to the sterilization station through the AGV at the transferring station for sterilization.

13. A control method for the fully automated filling line for tissue culture flasks according to claim 3, comprising the following steps:

S00, inputting the to-be-cleaned tissue culture flask boxes into the working range of the flask loading station through the material loading and conveying line, and transferring the tissue culture flasks to the flask sorting apparatus at the flask sorting station in batches through the flask loading mechanical arm at the flask loading station; and conveying, after the tissue culture flasks are completely removed from the material boxes of the tissue culture flask boxes, the material boxes to one side of the transferring station through the box loading and conveying line;

S10, sequentially inputting the tissue culture flasks into the flask righting station through the flask sorting apparatus; and transferring the material boxes on the box loading and conveying line to the transferring station through the material unloading mechanical arm at the material unloading station;

S20, detecting postures of the passing tissue culture flasks through the flask righting station, marking the fallen tissue culture flask, and pushing the fallen tissue culture flask out through the execution component when the fallen tissue culture flask moves to the preset position;

S30, performing degreasing on the tissue culture flasks detected as qualified through the degreasing apparatus at the degreasing station;

S40, performing external cleaning on the degreased tissue culture flasks through the external cleaning apparatus at the external cleaning station;

S50, performing internal cleaning on the externally cleaned tissue culture flasks through the internal cleaning apparatus at the internal cleaning station;

S60, performing filling on the internally cleaned tissue culture flasks through the filling apparatus at the filling station;

S70, performing cap placing and screwing on the filled tissue culture flasks through the cap screwing apparatus at the cap screwing station, with caps provided by the cap screwing apparatus through the cap placing apparatus at the cap placing station;

S80, transferring the tissue culture flasks after cap screwing to the material boxes at the transferring station in batches through the material unloading mechanical arm at the material unloading station; and S90, transferring the material boxes filled with the tissue culture flasks to the sterilization station through the AGV at the transferring station for sterilization.

14. A control method for the fully automated filling line for tissue culture flasks according to claim 4, comprising the following steps:

S00, inputting the to-be-cleaned tissue culture flask boxes into the working range of the flask loading station through the material loading and conveying line, and transferring the tissue culture flasks to the flask sorting apparatus at the flask sorting station in batches through the flask loading mechanical arm at the flask loading station; and conveying, after the tissue culture flasks are completely removed from the material boxes of the tissue culture flask boxes, the material boxes to one side of the transferring station through the box loading and conveying line;

S10, sequentially inputting the tissue culture flasks into the flask righting station through the flask sorting apparatus; and transferring the material boxes on the box loading and conveying line to the transferring station through the material unloading mechanical arm at the material unloading station;

S20, detecting postures of the passing tissue culture flasks through the flask righting station, marking the fallen tissue culture flask, and pushing the fallen tissue culture flask out through the execution component when the fallen tissue culture flask moves to the preset position;

S30, performing degreasing on the tissue culture flasks detected as qualified through the degreasing apparatus at the degreasing station;

S40, performing external cleaning on the degreased tissue culture flasks through the external cleaning apparatus at the external cleaning station;

S50, performing internal cleaning on the externally cleaned tissue culture flasks through the internal cleaning apparatus at the internal cleaning station;

S60, performing filling on the internally cleaned tissue culture flasks through the filling apparatus at the filling station;

S70, performing cap placing and screwing on the filled tissue culture flasks through the cap screwing apparatus at the cap screwing station, with caps provided by the cap screwing apparatus through the cap placing apparatus at the cap placing station;

S80, transferring the tissue culture flasks after cap screwing to the material boxes at the transferring station in batches through the material unloading mechanical arm at the material unloading station; and S90, transferring the material boxes filled with the tissue culture flasks to the sterilization station through the AGV at the transferring station for sterilization.

15. A control method for the fully automated filling line for tissue culture flasks according to claim 5, comprising the following steps:

S00, inputting the to-be-cleaned tissue culture flask boxes into the working range of the flask loading station through the material loading and conveying line, and transferring the tissue culture flasks to the flask sorting apparatus at the flask sorting station in batches through the flask loading mechanical arm at the flask loading station; and conveying, after the tissue culture flasks are completely removed from the material boxes of the tissue culture flask boxes, the material boxes to one side of the transferring station through the box loading and conveying line;

S10, sequentially inputting the tissue culture flasks into the flask righting station through the flask sorting apparatus; and transferring the material boxes on the box loading and conveying line to the transferring station through the material unloading mechanical arm at the material unloading station;

S20, detecting postures of the passing tissue culture flasks through the flask righting station, marking the fallen tissue culture flask, and pushing the fallen tissue culture flask out through the execution component when the fallen tissue culture flask moves to the preset position;

S30, performing degreasing on the tissue culture flasks detected as qualified through the degreasing apparatus at the degreasing station;

S40, performing external cleaning on the degreased tissue culture flasks through the external cleaning apparatus at the external cleaning station;

S50, performing internal cleaning on the externally cleaned tissue culture flasks through the internal cleaning apparatus at the internal cleaning station;

S60, performing filling on the internally cleaned tissue culture flasks through the filling apparatus at the filling station;

S70, performing cap placing and screwing on the filled tissue culture flasks through the cap screwing apparatus at the cap screwing station, with caps provided by the cap screwing apparatus through the cap placing apparatus at the cap placing station;

S80, transferring the tissue culture flasks after cap screwing to the material boxes at the transferring station in batches through the material unloading mechanical arm at the material unloading station; and S90, transferring the material boxes filled with the tissue culture flasks to the sterilization station through the AGV at the transferring station for sterilization.

16. A control method for the fully automated filling line for tissue culture flasks according to claim 6, comprising the following steps:

S00, inputting the to-be-cleaned tissue culture flask boxes into the working range of the flask loading station through the material loading and conveying line, and transferring the tissue culture flasks to the flask sorting apparatus at the flask sorting station in batches through the flask loading mechanical arm at the flask loading station; and conveying, after the tissue culture flasks are completely removed from the material boxes of the tissue culture flask boxes, the material boxes to one side of the transferring station through the box loading and conveying line;

S10, sequentially inputting the tissue culture flasks into the flask righting station through the flask sorting apparatus; and transferring the material boxes on the box loading and conveying line to the transferring station through the material unloading mechanical arm at the material unloading station;

S20, detecting postures of the passing tissue culture flasks through the flask righting station, marking the fallen tissue culture flask, and pushing the fallen tissue culture flask out through the execution component when the fallen tissue culture flask moves to the preset position;

S30, performing degreasing on the tissue culture flasks detected as qualified through the degreasing apparatus at the degreasing station;

S40, performing external cleaning on the degreased tissue culture flasks through the external cleaning apparatus at the external cleaning station;

S50, performing internal cleaning on the externally cleaned tissue culture flasks through the internal cleaning apparatus at the internal cleaning station;

S60, performing filling on the internally cleaned tissue culture flasks through the filling apparatus at the filling station;

S70, performing cap placing and screwing on the filled tissue culture flasks through the cap screwing apparatus at the cap screwing station, with caps provided by the cap screwing apparatus through the cap placing apparatus at the cap placing station;

S80, transferring the tissue culture flasks after cap screwing to the material boxes at the transferring station in batches through the material unloading mechanical arm at the material unloading station; and S90, transferring the material boxes filled with the tissue culture flasks to the sterilization station through the AGV at the transferring station for sterilization.

17. A control method for the fully automated filling line for tissue culture flasks according to claim 7, comprising the following steps:

S00, inputting the to-be-cleaned tissue culture flask boxes into the working range of the flask loading station through the material loading and conveying line, and transferring the tissue culture flasks to the flask sorting apparatus at the flask sorting station in batches through the flask loading mechanical arm at the flask loading station; and conveying, after the tissue culture flasks are completely removed from the material boxes of the tissue culture flask boxes, the material boxes to one side of the transferring station through the box loading and conveying line;

S10, sequentially inputting the tissue culture flasks into the flask righting station through the flask sorting apparatus; and transferring the material boxes on the box loading and conveying line to the transferring station through the material unloading mechanical arm at the material unloading station;

S20, detecting postures of the passing tissue culture flasks through the flask righting station, marking the fallen tissue culture flask, and pushing the fallen tissue culture flask out through the execution component when the fallen tissue culture flask moves to the preset position;

S30, performing degreasing on the tissue culture flasks detected as qualified through the degreasing apparatus at the degreasing station;

S40, performing external cleaning on the degreased tissue culture flasks through the external cleaning apparatus at the external cleaning station;

S50, performing internal cleaning on the externally cleaned tissue culture flasks through the internal cleaning apparatus at the internal cleaning station;

S60, performing filling on the internally cleaned tissue culture flasks through the filling apparatus at the filling station;

S70, performing cap placing and screwing on the filled tissue culture flasks through the cap screwing apparatus at the cap screwing station, with caps provided by the cap screwing apparatus through the cap placing apparatus at the cap placing station;

S80, transferring the tissue culture flasks after cap screwing to the material boxes at the transferring station in batches through the material unloading mechanical arm at the material unloading station; and S90, transferring the material boxes filled with the tissue culture flasks to the sterilization station through the AGV at the transferring station for sterilization.

18. A control method for the fully automated filling line for tissue culture flasks according to claim 8, comprising the following steps:

S00, inputting the to-be-cleaned tissue culture flask boxes into the working range of the flask loading station through the material loading and conveying line, and transferring the tissue culture flasks to the flask sorting apparatus at the flask sorting station in batches through the flask loading mechanical arm at the flask loading station; and conveying, after the tissue culture flasks are completely removed from the material boxes of the tissue culture flask boxes, the material boxes to one side of the transferring station through the box loading and conveying line;

S10, sequentially inputting the tissue culture flasks into the flask righting station through the flask sorting apparatus; and transferring the material boxes on the box loading and conveying line to the transferring station through the material unloading mechanical arm at the material unloading station;

S20, detecting postures of the passing tissue culture flasks through the flask righting station, marking the fallen tissue culture flask, and pushing the fallen tissue culture flask out through the execution component when the fallen tissue culture flask moves to the preset position;

S30, performing degreasing on the tissue culture flasks detected as qualified through the degreasing apparatus at the degreasing station;

S40, performing external cleaning on the degreased tissue culture flasks through the external cleaning apparatus at the external cleaning station;

S50, performing internal cleaning on the externally cleaned tissue culture flasks through the internal cleaning apparatus at the internal cleaning station;

S60, performing filling on the internally cleaned tissue culture flasks through the filling apparatus at the filling station;

S70, performing cap placing and screwing on the filled tissue culture flasks through the cap screwing apparatus at the cap screwing station, with caps provided by the cap screwing apparatus through the cap placing apparatus at the cap placing station;

S80, transferring the tissue culture flasks after cap screwing to the material boxes at the transferring station in batches through the material unloading mechanical arm at the material unloading station; and S90, transferring the material boxes filled with the tissue culture flasks to the sterilization station through the AGV at the transferring station for sterilization.

19. A control method for the fully automated filling line for tissue culture flasks according to claim 9, comprising the following steps:

S00, inputting the to-be-cleaned tissue culture flask boxes into the working range of the flask loading station through the material loading and conveying line, and transferring the tissue culture flasks to the flask sorting apparatus at the flask sorting station in batches through the flask loading mechanical arm at the flask loading station; and conveying, after the tissue culture flasks are completely removed from the material boxes of the tissue culture flask boxes, the material boxes to one side of the transferring station through the box loading and conveying line;

S10, sequentially inputting the tissue culture flasks into the flask righting station through the flask sorting apparatus; and transferring the material boxes on the box loading and conveying line to the transferring station through the material unloading mechanical arm at the material unloading station;

S20, detecting postures of the passing tissue culture flasks through the flask righting station, marking the fallen tissue culture flask, and pushing the fallen tissue culture flask out through the execution component when the fallen tissue culture flask moves to the preset position;

S30, performing degreasing on the tissue culture flasks detected as qualified through the degreasing apparatus at the degreasing station;

S40, performing external cleaning on the degreased tissue culture flasks through the external cleaning apparatus at the external cleaning station;

S50, performing internal cleaning on the externally cleaned tissue culture flasks through the internal cleaning apparatus at the internal cleaning station;

S60, performing filling on the internally cleaned tissue culture flasks through the filling apparatus at the filling station;

S70, performing cap placing and screwing on the filled tissue culture flasks through the cap screwing apparatus at the cap screwing station, with caps provided by the cap screwing apparatus through the cap placing apparatus at the cap placing station;

S80, transferring the tissue culture flasks after cap screwing to the material boxes at the transferring station in batches through the material unloading mechanical arm at the material unloading station; and S90, transferring the material boxes filled with the tissue culture flasks to the sterilization station through the AGV at the transferring station for sterilization.

* * * * *